United States Patent [19]

Patel et al.

[11] Patent Number: 5,041,630

[45] Date of Patent: Aug. 20, 1991

[54] WELL CEMENT SLURRIES AND DISPERSANTS THEREFOR

[75] Inventors: Bharat Patel; Michael Stephens, both of Bartlesville, Okla.

[73] Assignee: Phillips Petroleum Company, Bartlesville, Okla.

[21] Appl. No.: 491,964

[22] Filed: Mar. 12, 1990

Related U.S. Application Data

[62] Division of Ser. No. 299,661, Jan. 23, 1989, Pat. No. 4,923,516.

[51] Int. Cl.$^5$ ............................................ C07C 143/42
[52] U.S. Cl. .................................................... 562/41
[58] Field of Search .................... 568/34; 423/499; 562/41, 42

[56] References Cited

U.S. PATENT DOCUMENTS

| | | | |
|---|---|---|---|
| 3,479,287 | 11/1969 | Floyd et al. | 252/8.511 |
| 3,537,991 | 11/1970 | Parker | 252/8.5 |
| 3,956,140 | 5/1976 | Nahm et al. | 252/8.511 |
| 3,973,904 | 8/1976 | Endres et al. | 8/94.24 |
| 4,093,645 | 6/1978 | Davidson et al. | 562/41 |
| 4,131,582 | 12/1978 | Kako et al. | 524/457 |
| 4,293,342 | 10/1981 | Detroit | 166/293 |
| 4,325,890 | 4/1982 | Reitz et al. | 562/41 |
| 4,389,320 | 6/1983 | Clampitt | 252/8.551 |
| 4,469,604 | 9/1984 | Stapp et al. | 252/8.554 |
| 4,507,211 | 3/1985 | Naylor et al. | 562/41 |
| 4,632,786 | 12/1986 | Stapp et al. | 562/42 |

*Primary Examiner*—Olik Chaudhuri
*Assistant Examiner*—Andrew Griffis
*Attorney, Agent, or Firm*—Laney, Dougherty, Hessin & Beavers

[57] ABSTRACT

Well cement slurries, water soluble dispersants therefor and methods of producing the dispersants are provided. The dispersants prevent high initial cement slurry viscosities and friction losses when the slurries are pumped, and are comprised of water soluble sulfoalkylated naphthols in which the naphthol molecules are alkylated with at least one group having the formula $-C(R)_2-SO_3M$ wherein R is selected from hydrogen and alkyl radicals containing from 1 to 5 carbon atoms and M is an alkali metal.

7 Claims, No Drawings

WELL CEMENT SLURRIES AND DISPERSANTS THEREFOR

This is a divisional of copending application Ser. No. 07/299,661 filed on Jan 23, 1989; now U.S. Pat. No. 4,923,516 issued May 8, 1990.

BACKGROUND OF THE INVENTION

1. Field of the Invention

The present invention is generally directed to aqueous cement slurries used in oil and gas well operations, and more particularly, to such slurries containing dispersants which function to prevent premature slurry gelation and high viscosity development.

2. Description of the Prior Art

Aqueous cement slurries are commonly utilized in the oil industry in the completion, stimulation and production of oil and gas wells. The most common use of such aqueous cement slurries is in the bonding of conduits such as casing and liners disposed in the well bores to surrounding earth formations. Typically, an aqueous cement slurry is pumped down the inside of a conduit disposed in a well bore to the bottom of the well bore and then upwardly within the annular space between the outside of the conduit and the well bore. Upon hardening, the cement composition bonds the conduit to the earth formations forming the sides of the well bore.

A problem persistently encountered in pumping cement slurries through conduits disposed in well bores involves the premature gelation of the cement slurries whereby the slurries develop high viscosity rendering them difficult or impossible to pump.

Numerous additives have been developed and used heretofore which when combined with aqueous cement slurries function to retard early gelation and viscosity development. For example, U.S. Pat. No. 4,293,342 issued Oct. 6, 1981 discloses additives comprised of lingosulfonate derivatives which are useful as cement slurry gelation retarding agents. While such agents and other prior art dispersants are useful for retarding premature gelation and viscosity development in aqueous cement slurries, there is a continuous demand for more effective and economical such additives.

By the present invention, improved cement slurry dispersants are provided which retard premature gelation and viscosity development in aqueous cement slurries whereby the pumping times of such slurries are increased.

SUMMARY OF THE INVENTION

In one aspect of the present invention, dispersants for use in aqueous cement slurries are provided. When added to aqueous cement slurries, the dispersants retard the gelation and viscosity development of the slurries whereby friction losses during pumping are reduced. The cement slurry dispersants are basically comprised of a water soluble sulfoalkylated naphthol in which the naphthol molecule is alkylated with at least one group having the formula $-C(R)_2-SO_3M$ wherein R is selected from hydrogen and alkyl radicals containing from 1 to 5 carbon atoms and M is an alkali metal. A water soluble compound of chromium can optionally be admixed with the sulfoalkylated naphthol.

In another aspect of the present invention, a method of preparing the above-described cement dispersants is provided. In accordance with the method, $\alpha$-naphthol is reacted in an alkaline aqueous medium under reaction conditions with the product formed by reacting a carbonyl compound selected from aldehydes and ketones containing from 2 to 6 carbon atoms with a sulfur compound selected from sulfurous acid and water soluble salts thereof. To the resulting reaction mixture at reaction conditions is added a sufficient quantity of alkali metal hydroxide to condense the sulfoalkylated naphthol reaction product therewith and impact water solubility to the product. The resultant reaction product mixture can be dried to produce a solid water soluble sulfoalkylated naphthol dispersant.

In yet another aspect of the present invention, well cement slurries comprised of water, cement and the abovedescribed sulfoalkylated naphthol dispersants are provided.

It is, therefore, a general object of the present invention to provide well cement slurries and dispersants therefor.

A further object of the present invention is the provision of water soluble sulfoalkylated naphthol compounds useful as cement slurry dispersants and methods of preparing such compounds.

Another object of the present invention is the provision of aqueous cement slurry dispersants and cement slurries containing such dispersants which function to retard the early gelation and viscosity development of the slurries whereby increased slurry pumping times result.

Other and further objects, features and advantages of the present invention will be readily apparent to those skilled in the art upon a reading of the description of preferred embodiments which follows.

DESCRIPTION OF THE PREFERRED EMBODIMENTS

By the present invention, dispersants are provided which when added to aqueous cement slurries function to retard early gelation and the accompanying increase in viscosity. The dispersants are comprised of water soluble sulfoalkylated naphthol compounds in which the naphthol molecule is alkylated with at least one group having the formula $-C(R)_2-SO_3M$ wherein R is selected from hydrogen and alkyl radicals containing from 1 to 5 carbon atoms and M is an alkali metal.

The sulfoalkylated naphthol compounds can be utilized and are effective as dispersants by themselves in aqueous cement slurries, or the compounds can be utilized in admixture with water soluble inorganic compounds of chromium to provide additives of increased overall effectiveness. While a variety of inorganic chromium compounds can be utilized, particularly suitable such compounds are those selected from the group consisting of alkali metal and ammonium chromates and dichromates, e.g., sodium chromate, ammonium dichromate, etc.

In preparing the water soluble sulfoalkylated naphthol compounds of this invention, $\alpha$-naphthol is reacted in an alkaline aqueous medium under reaction conditions with the product formed by reacting a carbonyl compound selected from aldehydes and ketones containing from 2 to 6 carbon atoms with a sulfur compound selected from sulfurous acid and water soluble salts thereof. The resulting sulfoalkylated naphthol reaction product is condensed with a sufficient quantity of alkali metal hydroxide at reaction conditions to impart water solubility to the product. The sulfoalkylated naphthol product can be recovered as a dried solid from the reaction mixture using any suitable technique, such as by evaporation, drum drying or spray drying.

The alkaline aqueous medium in which the reaction is carried out is preferably an aqueous solution of an alkali metal hydroxide. The alkali metal hydroxide utilized in the condensation reaction to impart water solubility to the sulfoalkylated naphthol produced is preferably in the form of an aqueous alkali metal hydroxide solution, e.g., a 50% by weight sodium hydroxide solution. The most preferred alkali metal hydroxide for both the aqueous reaction medium and the condensation reaction is sodium hydroxide.

The aldehyde or ketone carbonyl compound containing from 2 to 6 carbon atoms utilized in the preparation of the sulfoalkylated naphthol can be represented by the formula $(R)_2C=O$ wherein R is selected from hydrogen and alkyl radicals containing from 1 to 5 carbon atoms, more preferably 1 to 3 carbon atoms. Examples of preferred such aldehydes and ketones include formaldehyde, aceraldehyde, propionaldehyde, acetone, methylethyl ketone, diethyl ketone, etc. Most preferably, the carbonyl compound is formaldehyde.

The sulfur compound used can be sulfurous acids and/or the water soluble salts of sulfurous acids. Particularly suitable salts are the alkali metal and ammonium sulfites and bisulfites. When a bisulfite or sulfurous acid is added to the alkaline reaction medium, it will be converted to a sulfite. The most preferred sulfur compound is sodium bisulfite.

In a preferred method of preparing the water soluble sulfoalkylated naphthol compounds of this invention, the carbonyl compound and the sulfur compound are pre-reacted followed by reaction with the -naphthol compound in an alkaline aqueous medium. For example, the aldehyde or ketone, the sulfur compound and water can be pre-reacted by stirring in a closed container. The naphthol is added to an alkaline aqueous reaction medium, e.g., an aqueous solution of alkali metal hydroxide, and the pre-reacted carbonyl compound and aldehyde or ketone are combined with the naphthol solution. The resulting mixture is heated for an initial reaction time sufficient to produce a sulfoalkylated naphthol product. The sulfoalkylated naphthol reaction product is next condensed with an alkali metal hydroxide to impart water solubility to the product. That is, small quantities of an aqueous alkali metal hydroxide solution are added to the reaction mixture at reaction conditions and allowed to react therewith until the alkali metal hydroxide solution can be added without precipitate formation. This condensation reaction between the initially formed sulfoalkylated naphthol reaction product and alkali metal hydroxide is necessary to produce a water soluble sulfoalkylated naphthol product. Upon completion of the condensation reaction, the reaction mixture can be dried to form a solid water soluble dispersant of the present invention.

The amounts of the above described reactants are generally not critical so long as a significant amount of each of the reactants is present. Preferably, stoichiometric equivalent amounts of the reactants are utilized. The particular amount of alkali metal hydroxide required to impart water solubility to the sulfoalkylated naphthol reaction product depends on various factors including the particular reaction conditions utilized and the alkalinity of the initial reaction medium. Preferably, the same alkali metal hydroxide is utilized in the aqueous reaction medium as is used in the condensation reaction. The amount of alkali metal hydroxide utilized in the alkaline aqueous reaction medium is preferably an amount which results in a medium pH of from about 10 to about 13. As stated above, the particular amount of alkali metal hydroxide utilized in the condensation reaction is that amount required to make the reaction product water soluble.

All of the reactions involved in preparing the water soluble sulfoalkylated naphthol compounds will take place at ordinary room temperature, but at a reduced rate. As a practical matter, it is preferred to employ elevated temperatures to cause the reactions to take place in less time. As a general rule, temperatures in the order of 125° F. to 212° F. are sufficient. However, a more preferred range is from about 180° F. to about 210° F. If desired, the reaction mixture can be refluxed at atmospheric pressure, or the reaction mixture can be heated in an autoclave under superatmospheric pressure to obtain higher temperatures and more rapid reaction rates. The maximum temperatures employed will usually be in the order of 300° F. The reaction time, as mentioned, will be dependent upon the reaction temperature employed and ranges from about 0.5 to about 10 hours.

When a water soluble inorganic compound of chromium is utilized in admixture with the water soluble sulfoalkylated naphthol compound, the weight ratio of dry solid sulfoalkylated naphthol to chromium compound in the mixture is in the range of from about 12:1 to about 2:1, most preferably within the range of from about 9:1 to about 5:1. The presence of the water soluble inorganic chromium compound in admixture with the sulfoalkylated naphthol compound imparts additional stability to the rheological properties of cement slurries to which the mixture is added.

The well cement slurries of the present invention are comprised of water, cement and the above-described water soluble sulfoalkylated naphthol compounds, or such compounds in admixture with one or more of the water soluble chromium compounds described above. The water used can be any of the various forms of water commonly used to produce oilfield aqueous cement slurries including fresh water, brines and seawater. The cements can be any of the hydraulic cements commonly used as, for example, any of the API Classes A through J cements. The cement slurries can include other components such as water loss control additives, extenders, fillers, strength enhancers and the like.

The amount of sulfoalkylated naphthol dispersant of the invention utilized in a cement slurry, either with or without a chromium compound in admixture therewith will generally fall within the broad range of from about 0.1% to about 3.5% of dispersant by weight of dry cement used to form the slurry. Preferably, the dispersant is combined with a cement slurry in an amount in the range of from about 0.2% to about 1.5% by weight of dry cement used therein. The particular manner in which the dispersant is combined with the cement slurry is not critical.

In order to further illustrate the present invention, the following examples are given.

EXAMPLE 1

In a closed container, 21.7 grams of sodium bisulfite, 20 milliliters of water and 16.88 milliliters of a 37% aqueous solution of formaldehyde were reacted with continuous stirring for about one hour. In a beaker, 30 grams of α-naphthol (99+% pure) and 30 milliliters of de-ionized water were mixed together. 5 milliliters of an aqueous sodium hydroxide solution (1 ml. contained 0.5 g NaOH) were added to the mixture. The mixture was heated to 200° F. while continuously being stirred, and after additional stirring for 15 minutes at 200° F., the previously reacted formaldehyde-sodium bisulfite mixture was added. The resulting reaction mixture was allowed to react for about two hours at 200° F. At the end of the reaction time, the reaction mixture contained an insoluble black sticky mass. Upon the addition of additional aqueous sodium hydroxide solution, the water insoluble gummy mass continued to react, and after a total of 16 milliliters of additional sodium hydroxide solution were added, the gummy mass was dissolved. The reaction mixture was dried and the dried residue was ground.

EXAMPLE 2

The procedure of Example 1 was repeated except that sodium formaldehyde bisulfite powder (Practical grade, lot #A13A from Eastman Kodak Company, Rochester, N.Y.) was used in place of the formaldehyde-sodium bisulfite mixture in the initial sulfoalkylation reaction. The particular procedure followed was that 21.63 grams of o-naphthol were combined with 50 milliliters of de-ionized water and heated to about 175° F. 3 milliliters of an aqueous sodium hydroxide solution (1 ml contained 0.5 g NaOH) were added, and the resulting mixture was heated to about 200° F. After maintaining at 200° F. for 10 minutes, 20.1 grams of sodium formaldehydebisulfite powder were added. The resulting mixture was heated at about 215° F. for approximately 2½ hours. To the resulting reaction mixture, 11 milliliters of an aqueous sodium hydroxide solution (1 ml contained 0.5 g NaOH) were added over a time period of about 5 minutes while heating at about 215° F. to condense the sodium hydroxide with the sulfoalkylated naphthol reaction product. After heating another 10 minutes the reaction mixture did not contain any undissolved material. The reaction mixture was dried in an oven at about 220° F. to obtain a solid water-soluble sulfoalkylated naphthol product.

EXAMPLE 3

The procedure of Example 2 was repeated except that the quantity of sodium hydroxide solution utilized as the alkaline aqueous reaction medium was increased to an amount equal to the total used in Example 2, i.e., 14 milliliters of aqueous sodium hydroxide solution (1 ml contained 0.5 g NaOH). More particularly, 21.63 grams of α-naphthol were combined with 50 milliliters of de-ionized water and heated to about 175° F. 14 milliliters of the same sodium hydroxide solution were added, and the resulting mixture was heated to about 200° F. After maintaining at 200° F. for 10 minutes, 20.1 grams of sodium formaldehyde bisulfite powder were added. The resulting mixture was heated at about 215° F. for approximately 3 hours. The resulting reaction mixture contained an undissolved gummy mass. After cooling the mixture to about 120° F., the gummy mass was cut into small pieces. The pieces of gummy mass were dried at about 220° F. and ground.

EXAMPLE 4

A cement slurry comprised of 329.2 grams of fresh water and 851.3 grams of Trinity API Class H cement was prepared having a density of 16.4 pounds per gallon, a volume of 1.06 cubic feet per sack of cement used and a water quantity equivalent to 4.36 gallons per sack.

The rheology at 80° F. of the cement slurry without the sulfoalkylated naphthol dispersant of this invention was determined using a FANN Model 35 Viscometer in accordance with API Specification 10, Appendix H, First addition, Jan. 1982.

4.257 grams of solid water soluble sulfoalkylated naphthol dispersant, prepared as described in Examples 1, 2 and 3 above, were combined with 851.3 gram portions of dry API Class H cement. The resulting dry blends were then each added to 326.2 grams of fresh water and mixed in accordance with API Specification 10, Section 5. The resultant cement slurries contained 0.5% of the dispersant by weight of dry cement in the slurries. The rheologies of the cement slurries containing the dispersants were determined in the same manner as described for the cement slurry without dispersant. The results of the rheology determinations are given in Table I below.

TABLE I

| Cement Slurry, grams Cement/ grams H₂O | Quantity of Sulfoalkylated Naphthol Dispersant Added, grams | Source of Sulfo- alkylated Naphthol | Rheology Viscometer[1] Readings at 80° F. | | | | | |
|---|---|---|---|---|---|---|---|---|
| | | | 600 rpm | 300 rpm | 200 rpm | 100 rpm | 6 rpm | 3 rpm |
| 2.6/1 (851.3/326.2) | None | — | 164 | 133 | 112 | 86 | 25 | 20 |
| 2.6/1 | 4.257 | Example 1 | 69 | 32 | 20 | 10 | 2 | 1 |
| 2.6/1 | 4.257 | Example 2 | 87 | 43 | 34 | 25 | 12 | 10 |
| 2.6/1 | 4.257 | Example 3 | 90 | 45 | 35 | 26 | 12 | 11 |

[1]No. 1 Bob, rotor and Spring combination

From Table I it can be seen that the dispersant of the present invention is effective in reducing the rheology of an aqueous cement slurry and thereby increasing the pumping time of the slurry.

The present invention, therefore, is well adapted to carry out the objects and attain the ends and advantages mentioned as well as those inherent therein. While numerous changes in the quantities of components and other variables of the present invention can be made by those skilled in the art, such changes are encompassed within the spirit of this invention as defined by the appended claims.

What is claimed is:

1. A method of preparing a water soluble sulfoalkylated naphthol compound useful as a cement slurry dispersant comprising the steps of:
   (a) reacting α-naphthol, in an alkaline aqueous medium under reaction conditions, with the product formed by reacting a carbonyl compound selected from aldehyde and ketones containing from 2 to 6 carbon atoms with a sulfur compound selected from sulfurous acid and water soluble salts thereof; and then
   (b) adding a sufficient quantity of alkali metal hydroxide to the resulting reaction mixture of step (a) at reaction conditions to condense a sulfoalkylated naphthol reaction product therewith and impart water solubility to said sulfoalkylated naphthol reaction product.

2. The method of claim 1 wherein said alkaline aqueous medium is an aqueous solution of an alkali metal hydroxide.

3. The method of claim 2 wherein said alkali metal hydroxide added in step (b) is added in the form of an aqueous alkali metal hydroxide solution.

4. The method of claim 3 wherein said alkali metal hydroxide is sodium hydroxide.

5. The method of claim 4 wherein said carbonyl compound is formaldehyde.

6. The method of claim 5 wherein said sulfur compound is sodium bisulfite.

7. The method of claim 6 which is further characterized to include the step of drying said resultant reaction mixture to produce a solid water soluble sulfoalkylated naphthol dispersant product.

* * * * *